United States Patent
Nguyen

(10) Patent No.: US 9,555,071 B2
(45) Date of Patent: Jan. 31, 2017

(54) METHODS AND COMPOSITIONS FOR THE TREATMENT OF AXONAL AND NEURONAL DEGENERATION

(71) Applicant: Thien Nguyen, Potomac, MD (US)

(72) Inventor: Thien Nguyen, Potomac, MD (US)

( * ) Notice: Subject to any disclaimer, the term of this patent is extended or adjusted under 35 U.S.C. 154(b) by 0 days.

(21) Appl. No.: 13/917,203

(22) Filed: Jun. 13, 2013

(65) Prior Publication Data
US 2013/0338075 A1    Dec. 19, 2013

Related U.S. Application Data

(60) Provisional application No. 61/659,159, filed on Jun. 13, 2012.

(51) Int. Cl.
| | |
|---|---|
| *C07K 5/09* | (2006.01) |
| *C07K 7/64* | (2006.01) |
| *A61K 38/08* | (2006.01) |
| *C07K 5/11* | (2006.01) |
| *C07K 7/06* | (2006.01) |
| *C07K 7/08* | (2006.01) |
| *C07K 14/00* | (2006.01) |
| *A61K 38/06* | (2006.01) |
| *A61K 38/07* | (2006.01) |
| *A61K 38/10* | (2006.01) |
| *A61K 38/12* | (2006.01) |
| *A61K 9/00* | (2006.01) |

(52) U.S. Cl.
CPC ............. *A61K 38/08* (2013.01); *A61K 9/0019* (2013.01); *A61K 38/06* (2013.01); *A61K 38/07* (2013.01); *A61K 38/10* (2013.01); *A61K 38/12* (2013.01); *C07K 5/0817* (2013.01); *C07K 5/1019* (2013.01); *C07K 7/06* (2013.01); *C07K 7/08* (2013.01); *C07K 7/64* (2013.01); *C07K 14/001* (2013.01)

(58) Field of Classification Search
CPC ............... C07K 5/08; C07K 5/10; C07K 7/06; C07K 7/64; C07K 14/001
See application file for complete search history.

(56) References Cited

U.S. PATENT DOCUMENTS

| 5,352,667 A | * | 10/1994 | Lider et al. ................... 514/21.9 |
| 5,554,601 A | | 9/1996 | Simpkins et al. |
| 5,629,294 A | * | 5/1997 | diZerega et al. .............. 514/7.4 |

OTHER PUBLICATIONS

Acharya et al., alpha-v Integrin expression by DCs is required for Th17 cell differentiation and development of experimental autoimmune encephalomyelitis in mice, Dec. 2010, The Journal of Clinical Investigation 120(12):4445-4452.*
Cao et al., "The Inhibition Site on Myelin-Associated Glycoprotein Is within Ig-Domain 5 and Is Distinct from the Sialic Acid Binding Site," The Journal of Neuroscience, 2007, vol. 27, Iss. 34, pp. 9146-9154.
Dashiell et al., "Myelin-associated glycoprotein modulates expression and phosphorylation of neuronal cytoskeletal elements and their associated kinases," Journal of Neurochemistry, 2002, vol. 81, Iss. 6, pp. 1263-1272.
Davies, "The Cyclization of Peptides and Depsipeptides," Journal of Peptide Science, 2003, vol. 9, Iss. 8, pp. 471-501.
Ebenezer et al., "Denervation of skin in neuropathies: the sequence of axonal and Schwann cell changes in skin biopsies," Brain, 2007, vol. 130, Iss. 10, pp. 2703-2714.
Fournier et al., "Rho Kinase Inhibition Enhances Axonal Regeneration in the Injured CNS," The Journal of Neuroscience, 2003, vol. 23, Iss. 4, pp. 1416-1423.
Garcia et al., "NF-M is an essential target for the myelin-directed "outside-in" signaling cascade that mediates radial axonal growth," The Journal of Cell Biology, 2003, vol. 163, No. 5, pp. 1011-1020.
Hsieh et al., "Regional Modulation of Neurofilament Organization by Myelination in Normal Axons," The Journal of Neuroscience, 1994, vol. 14, Iss. 11, pp. 6392-6401.
Krajewski et al., "Neurological dysfunction and axonal degeneration in Charcot—Marie—Tooth disease type 1A," Brain, 2000, vol. 123, Iss. 7, pp. 1516-1527.
Nguyen et al., "Axonal Protective Effects of the Myelin-Associated Glycoprotein," The Journal of Neuroscience, 2009, vol. 29, Iss. 3, pp. 630-637.
Oh et al., "Mechanisms of normal appearing corpus callosum injury related to pericallosal T1 lesions in multiple sclerosis using directional diffusion tensor and $^{1}$H MRS imaging ," Journal of Neurology, Neurosurgery & Psychiatry, 2004, vol. 75, Iss. 9, pp. 1281-1286.
Rao et al., "The neurofilament middle molecular mass subunit carboxyl-terminal tail domains is essential for the radial growth and cytoskeletal architecture of axons but not for regulating neurofilament transport rate," The Journal of Cell Biology, 2003, vol. 163, No. 5, pp. 1021-1031.
Tang et al., "Myelin-associated Glycoprotein Interacts with Neurons via a Sialic Acid Binding Site at ARG118 and a Distinct Neurite Inhibition Site," The Journal of Cell Biology, 1997, vol. 138, No. 6, pp. 1355-1366.
Trapp et al., "Axonal Transection in the Lesions of Multiple Sclerosis," The New England Journal of Medicine, 1998, vol. 338, No. 5, pp. 278-285.
Trapp et al., "Presence of the myelin-associated glycoprotein correlates with alterations in the periodicity of peripheral myelin,"The Journal of Cell Biology, 1982, vol. 92, No. 3, pp. 877-882.
Yin et al., "Myelin-Associated Glycoprotein Is a Myelin Signal that Modulates the Caliber of Myelinated Axons," The Journal of Neuroscience, 1998, vol. 18, Iss. 6, pp. 1953-1962.

* cited by examiner

*Primary Examiner* — John Ulm
(74) *Attorney, Agent, or Firm* — Sheridan Ross P.C.

(57) ABSTRACT

The present invention generally relates to methods and compositions for preventing or treating axonal and/or neuronal degeneration in a subject by administering a composition comprising a peptide that comprises the amino acid sequence Arginine-Glycine-Aspartate (RGD).

27 Claims, 5 Drawing Sheets

G

H

E

SEQUENCE LISTING

<160> NUMBER OF SEQ ID NOS: 19

<210> SEQ ID NO 1
<211> LENGTH: 5
<212> TYPE: PRT
<213> ORGANISM: ARTIFICIAL SEQUENCE
<220> FEATURE:
<223> OTHER INFORMATION: Synthetic Peptide, Linear or Cyclo

<400> SEQUENCE: 1

Arg Gly Asp Tyr Lys
1               5

<210> SEQ ID NO 2
<211> LENGTH: 5
<212> TYPE: PRT
<213> ORGANISM: ARTIFICIAL SEQUENCE
<220> FEATURE:
<223> OTHER INFORMATION: Synthetic Peptide, Linear or Cyclo

<400> SEQUENCE: 2

Gly Arg Gly Asp Ser
1               5

<210> SEQ ID NO 3
<211> LENGTH: 6
<212> TYPE: PRT
<213> ORGANISM: ARTIFICIAL SEQUENCE
<220> FEATURE:
<223> OTHER INFORMATION: Synthetic Peptide, Linear or Cyclo

<400> SEQUENCE: 3

Gly Arg Gly Asp Ser Pro
1               5

<210> SEQ ID NO 4
<211> LENGTH: 6
<212> TYPE: PRT
<213> ORGANISM: ARTIFICIAL SEQUENCE
<220> FEATURE:
<223> OTHER INFORMATION: Synthetic Peptide, Linear or Cyclo

<400> SEQUENCE: 4

Phe Arg Gly Asp Leu Gly
1               5

<210> SEQ ID NO 5
<211> LENGTH: 6
<212> TYPE: PRT
<213> ORGANISM: ARTIFICIAL SEQUENCE
<220> FEATURE:
<223> OTHER INFORMATION: Synthetic Peptide, Linear or Cyclo

<400> SEQUENCE: 5

Arg Arg Gly Asp Gln Thr
1               5

<210> SEQ ID NO 6
<211> LENGTH: 6
<212> TYPE: PRT
<213> ORGANISM: ARTIFICIAL SEQUENCE
<220> FEATURE:
<223> OTHER INFORMATION: Synthetic Peptide, Linear or Cyclo

<400> SEQUENCE: 6

Lys Arg Gly Asp Asn Phe
1               5

```
<210> SEQ ID NO 7
<211> LENGTH: 6
<212> TYPE: PRT
<213> ORGANISM: ARTIFICIAL SEQUENCE
<220> FEATURE:
<223> OTHER INFORMATION: Synthetic Peptide, Linear or Cyclo

<400> SEQUENCE: 7

Pro Arg Gly Asp Leu Thr
1               5

<210> SEQ ID NO 8
<211> LENGTH: 6
<212> TYPE: PRT
<213> ORGANISM: ARTIFICIAL SEQUENCE
<220> FEATURE:
<223> OTHER INFORMATION: Synthetic Peptide, Linear or Cyclo

<400> SEQUENCE: 8

Phe Arg Gly Asp Leu Pro
1               5

<210> SEQ ID NO 9
<211> LENGTH: 6
<212> TYPE: PRT
<213> ORGANISM: ARTIFICIAL SEQUENCE
<220> FEATURE:
<223> OTHER INFORMATION: Synthetic Peptide, Linear or Cyclo

<400> SEQUENCE: 9

Phe Arg Gly Asp Ser Pro
1               5

<210> SEQ ID NO 10
<211> LENGTH: 7
<212> TYPE: PRT
<213> ORGANISM: ARTIFICIAL SEQUENCE
<220> FEATURE:
<223> OTHER INFORMATION: Synthetic Peptide, Linear or Cyclo

<400> SEQUENCE: 10

Leu Arg Gly Asp Asn Pro Gln
1               5

<210> SEQ ID NO 11
<211> LENGTH: 7
<212> TYPE: PRT
<213> ORGANISM: ARTIFICIAL SEQUENCE
<220> FEATURE:
<223> OTHER INFORMATION: Synthetic Peptide, Linear or Cyclo

<400> SEQUENCE: 11

Glu Lys Arg Gly Asp Arg Glu
1               5

<210> SEQ ID NO 12
<211> LENGTH: 8
<212> TYPE: PRT
<213> ORGANISM: ARTIFICIAL SEQUENCE
<220> FEATURE:
<223> OTHER INFORMATION: Synthetic Peptide, Linear or Cyclo

<400> SEQUENCE: 12

Gly Phe Arg Gly Asp Gly Gln Thr
1               5
```

```
<210> SEQ ID NO 13
<211> LENGTH: 6
<212> TYPE: PRT
<213> ORGANISM: ARTIFICIAL SEQUENCE
<220> FEATURE:
<223> OTHER INFORMATION: Synthetic Peptide, Linear or Cyclo

<400> SEQUENCE: 13

Trp Arg Gly Asp Gly Arg
1               5

<210> SEQ ID NO 14
<211> LENGTH: 5
<212> TYPE: PRT
<213> ORGANISM: ARTIFICIAL SEQUENCE
<220> FEATURE:
<223> OTHER INFORMATION: Synthetic Peptide, Linear or Cyclo

<400> SEQUENCE: 14

Ala Arg Gly Asp Val
1               5

<210> SEQ ID NO 15
<211> LENGTH: 6
<212> TYPE: PRT
<213> ORGANISM: ARTIFICIAL SEQUENCE
<220> FEATURE:
<223> OTHER INFORMATION: Synthetic Peptide, Linear or Cyclo

<400> SEQUENCE: 15

Ile Arg Gly Asp Ser Pro
1               5

<210> SEQ ID NO 16
<211> LENGTH: 6
<212> TYPE: PRT
<213> ORGANISM: ARTIFICIAL SEQUENCE
<220> FEATURE:
<223> OTHER INFORMATION: Synthetic Peptide, Linear or Cyclo

<400> SEQUENCE: 16

Cys Arg Gly Asp Asn Gly
1               5

<210> SEQ ID NO 17
<211> LENGTH: 6
<212> TYPE: PRT
<213> ORGANISM: ARTIFICIAL SEQUENCE
<220> FEATURE:
<223> OTHER INFORMATION: Synthetic Peptide, Linear or Cyclo

<400> SEQUENCE: 17

Tyr Arg Gly Asp Thr Pro
1               5

<210> SEQ ID NO 18
<211> LENGTH: 5
<212> TYPE: PRT
<213> ORGANISM: Artificial Sequence
<220> FEATURE:
<223> OTHER INFORMATION: Synthetic Peptide, Linear or Cyclo

<400> SEQUENCE: 18

Arg Gly Asp Ser Pro
1               5
```

```
<210> SEQ ID NO 19
<211> LENGTH: 5
<212> TYPE: PRT
<213> ORGANISM: Artificial Sequence
<220> FEATURE:
<223> OTHER INFORMATION: Synthetic Peptide, Linear or Cyclo

<400> SEQUENCE: 19

Arg Gly Asp Leu Pro
1               5
```

METHODS AND COMPOSITIONS FOR THE TREATMENT OF AXONAL AND NEURONAL DEGENERATION

CROSS REFERENCE TO RELATED APPLICATIONS

This application claims the benefit of priority under 35 U.S.C. §119(e) from U.S. Provisional Application Ser. No. 61/659,159 filed on Jun. 13, 2012, the contents of which are incorporated herein in their entirety by this reference.

SEQUENCE LISTING

This application contains a Sequence Listing submitted electronically as a text file by EFS-Web. The text file, named "6837-1 Sequence Listing ST25", has a size in bytes of 4 KB, and was recorded on Jun. 13, 2013. The information contained in the text file is incorporated herein by reference in its entirety pursuant to 37 CFR §1.52(e)(5).

FIELD OF INVENTION

The present invention generally relates to methods, compositions and materials for treatment and prevention of axonal and neuronal degeneration and related nerve injury, toxic insults or neurodegenerative disorders.

BACKGROUND OF THE INVENTION

Neurodegenerative disorders are hereditary and sporadic conditions which are characterized by progressive nervous system dysfunction. These disorders are often associated with atrophy of the affected central or peripheral structures of the nervous system. They include diseases such as Alzheimer's Disease and other dementias, Brain Cancer, Degenerative Nerve Diseases, Encephalitis, Epilepsy, Genetic Brain Disorders, Head and Brain Malformations, Hydrocephalus, Stroke, Parkinson's Disease, Multiple Sclerosis, Amyotrophic Lateral Sclerosis (ALS or Lou Gehrig's Disease), Huntington's Disease, Prion Diseases, polyneuropathy, and others. Interventions include preventative measures, lifestyle changes, physiotherapy or other therapy, neuro-rehabilitation, pain management, medication, or operations performed by neurosurgeons (WHO Neurological Disorders: Public Health Challenges, 2006).

Axonal degeneration is a common hallmark of many neurodegenerative diseases. A longstanding clinical observation is the tendency for demyelinated nerve fibers to undergo degeneration and loss. There is now a wealth of evidence that demyelination contributes to altered axonal transport, axonal degeneration, and loss (de Waegh et al., 1992; Trapp et al., 1998; Coleman and Perry, 2002; Ciccarelli et al., 2003; Oh et al., 2004). Examples include heritable demyelinating diseases of both the CNS and PNS. Many of the genetic defects in these diseases are abnormalities in genes encoding intrinsic myelin proteins and not expressed in axons. The clinical manifestations are often attributable to progressive, distally predominant axonal degeneration (Berciano et al., 2000; Krajewski et al., 2000).

The myelin-associated glycoprotein (MAG) is a component of all myelinated internodes. MAG is a transmembrane glycoprotein containing five Ig-like domains in its extracellular domain. It is an adhesion molecule belonging to the immunoglobin superfamily. MAG is distinctively located in the adaxonal plasmalemma that apposes the axon as well as the paranodal loops, Schmidt-Lanterman incisures, and mesaxons (Trapp and Quarles, 1982). The normal role of MAG is not well understood. MAG is not necessary for myelination, and myelin sheaths of MAG knock-out mice (MAG−/−) are largely normal (Yin et al., 1998). Its distribution has prompted the hypothesis that MAG prevents compaction of myelin membranes and contributes to the uniform intermembranous distance characteristic of the periaxonal space (Trapp and Quarles, 1982). MAG is known to signal to the axon, locally influencing the phosphorylation of axonal neurofilaments immediately beneath MAG-bearing membranes because of reduced interfilament spacing (Hsieh et al., 1994; Dashiell et al., 2002). Myelinated axons of MAG−/− mice have smaller diameters than normal as a result of hypophosphorylation of the neurofilament proteins NF-H and NF-M (Garcia et al., 2003; Rao et al., 2003).

Much of the published research on MAG has focused on its ability to inhibit axonal growth and elongation during regeneration. Multiple axonal receptors have been proposed to mediate MAG-induced growth cone collapse. One is a multicomponent complex consisting of a ligand-binding Nogo-66 receptor (NgR) and two transmembrane coreceptors, LINGO-1 and either p75 or TROY (Fournier et al., 2003; Mi et al., 2004). A second is proposed to be gangliosides GD1a and GT1b. Interaction of MAG with axons involves at least two recognition sites on MAG: one around arginine 118 (R118) in Ig domain 1 and second in Ig domains 4 and 5 (Kelm et al., 1994; Tang et al., 1997; Cao et al., 2007). Whereas Ig domains 4 and 5 are believed to be important for the interaction with NgR, the R118 binding site is thought to involve in interactions with gangliosides. Other roles of MAG at the R118 binding site remain unclear.

MAG−/− mice develop axonal loss in the CNS and PNS (Yin et al., 1998; Pan et al., 2005) suggesting that MAG may influence axonal maintenance. A recent study indicated that MAG promotes axonal stability and survival in cell culture and in vivo (Nguyen et al., 2009). This study showed that MAG signals to the axon to promote stability of axonal microtubules, and promotes axonal survival in the face of insults such as vincristine, acrylamide, and inflammatory mediators. The effect of MAG on axonal stability is independent of Nogo signaling in the axon and depends on the arginine 118 residue in the RGD (Arginine-Glycine-Aspartate) domain of the extracellular segment of the molecule. An R118-mutated MAG failed to prevent axonal degeneration caused by vincristine. This suggested that MAG-induced axonal protection depends on the functional binding site around arginine 118.

Despite the axon protective abilities of MAG, its potential as a candidate drug in the treatment of neurodegenerative disorders is limited due to its high molecular weight which makes it unable to cross the blood-brain barrier in patients. There continues to be a pressing need in the art for novel therapies and molecules that exhibit neuronal and axonal protective effect and are effective in vivo, crossing the plasma membrane and the blood-brain barrier.

SUMMARY OF THE INVENTION

Peptides containing the RGD sequence and their derivatives prevent axonal and neuronal degeneration in cell culture and animals. Axonal loss accounts for a significant portion of the irreversible clinical deficits seen in patients with neurodegenerative diseases. These peptides provide novel therapeutic agents to treat and prevent progression and onset of clinical symptoms in neurodegenerative diseases characterized by axonal and neuronal degeneration.

In one embodiment, the present invention includes a method of preventing or treating axonal and/or neuronal degeneration in a subject who has or is at risk of having a condition involving axonal and/or neuronal degeneration, comprising administering to the subject a composition comprising a peptide, wherein the peptide is from about three to about fifty amino acids in length and comprises the amino acid sequence Arginine-Glycine-Aspartate (RGD).

In some embodiments, the subject is a mammal. In some embodiments, the step of administering is by a mode of administration selected from the group consisting of oral, parenteral, subcutaneous and intravenous administration.

In another embodiment, the present invention includes a composition for treatment of conditions involving axonal and/or neuronal degeneration comprising a peptide wherein the peptide is from about three to about fifty amino acids in length and comprises the amino acid sequence Arginine-Glycine-Aspartate (RGD).

In some embodiments, the condition is selected from the group consisting of nerve injury, toxic insult and neurodegenerative disorders. In some embodiments, the condition is a neurodegenerative disorder selected from the group consisting of: Charcot-Marie-Tooth, multiple sclerosis, Alzheimer's disease, chronic spinocerebellar degeneration, diabetes, stroke, brain ischemia, demyelinating disorder, polyneuropathy, Parkinson's disease, multiple system atrophy (MSA), motor neuron disease, dementia, and combinations thereof. In some embodiments, the Charcot-Marie-Tooth is selected from the group consisting of Charcot-Marie-Tooth type 1 and type 6. In some embodiments, the polyneuropathy is selected from the group consisting of Toxic polyneuropathy, diabetic polyneuropathy, drug induced polyneuropathy, autoimmune polyneuroapthy, demyelinating polyneuropathy, and inherited polyneuropathy. In some embodiments, the motor neuron disease is selected from the group consisting of amyotrophic lateral sclerosis (ALS), Huntington's disease and Spinal muscular atrophy. In some embodiments, the dementia is selected from the group consisting of temporal dementia and lewy body dementia. In some embodiments, the condition is a nerve injury. In some embodiments, the condition is a toxic insult.

In some embodiments, the composition further comprises a pharmaceutically acceptable carrier.

In another embodiment, the present invention includes a method of protecting axons and/or neurons from degeneration, comprising contacting the axons and/or neurons with a composition comprising a peptide, wherein the peptide is from about three to about fifty amino acids in length and comprises the amino acid sequence Arginine-Glycine-Aspartate (RGD).

In some embodiments, the peptide is from about three to about thirty amino acids long. In some embodiments, the peptide is from about three to about fifteen amino acids long. In some embodiments, the peptide is from about four to about eight amino acids in length. In some embodiments, the RGD sequence is capable of binding to beta-1-integrin protein.

In some embodiments, the peptide is cyclic. In some embodiments, the peptide comprises an amino acid sequence selected from the group consisting of (a) RGDYK (SEQ ID NO:1), GRGDS (SEQ ID NO:2), GRGDSP (SEQ ID NO:3), FRGDLG (SEQ ID NO:4), RRGDQT (SEQ ID NO:5), KRGDNF (SEQ ID NO:6), PRGDLT (SEQ ID NO:7), FRGDLP (SEQ ID NO:8), FRGDSP (SEQ ID NO:9), LRGDNPQ (SEQ ID NO:10), EKRGDRE (SEQ ID NO:11), GFRGDGQT (SEQ ID NO:12), WRGDGR (SEQ ID NO:13), ARGDV (SEQ ID NO:14), IRGDSP (SEQ ID NO:15), CRGDNG (SEQ ID NO:16) and YRGDTP (SEQ ID NO:17), (b) a conservatively modified variant of any of the foregoing amino acid sequences, and (c) an amino acid sequence that is at least about 70% identical to any of the foregoing amino acid sequences. In some embodiments, the peptide is selected from the group consisting of cyclo-RGDYK (SEQ ID NO:1), GRGDS (SEQ ID NO:2), FRGDLG (SEQ ID NO:4), FRGDLP (SEQ ID NO:8), RRGDQT (SEQ ID NO:5), KRGDNF (SEQ ID NO:6), cyclo-IRGDSP (SEQ ID NO:15), cylco-FRGDSP (SEQ ID NO:9), cyclo-FRGDLP (SEQ ID NO:8) and cyclo-GRGDSP (SEQ ID NO:3).

In some embodiments, the peptide is subjected to a modification selected from the group consisting of is pegylation, cyclization, N-terminal acetylation, C-terminal amidation, N-methylation, phosphorylation of amino acids, and peptide biotinylation. In some embodiments, the peptide comprises a fluorescent label. In some embodiments, the peptide comprises one or more modified amino acids. In some embodiments, the one or more modified amino acids are selected from the group consisting of D-amino-acids, L-beta-homo amino acids, D-beta-homo amino acids, N-methylated amino acids, and combinations thereof.

DETAILED DESCRIPTION OF THE INVENTION

Figure 1:
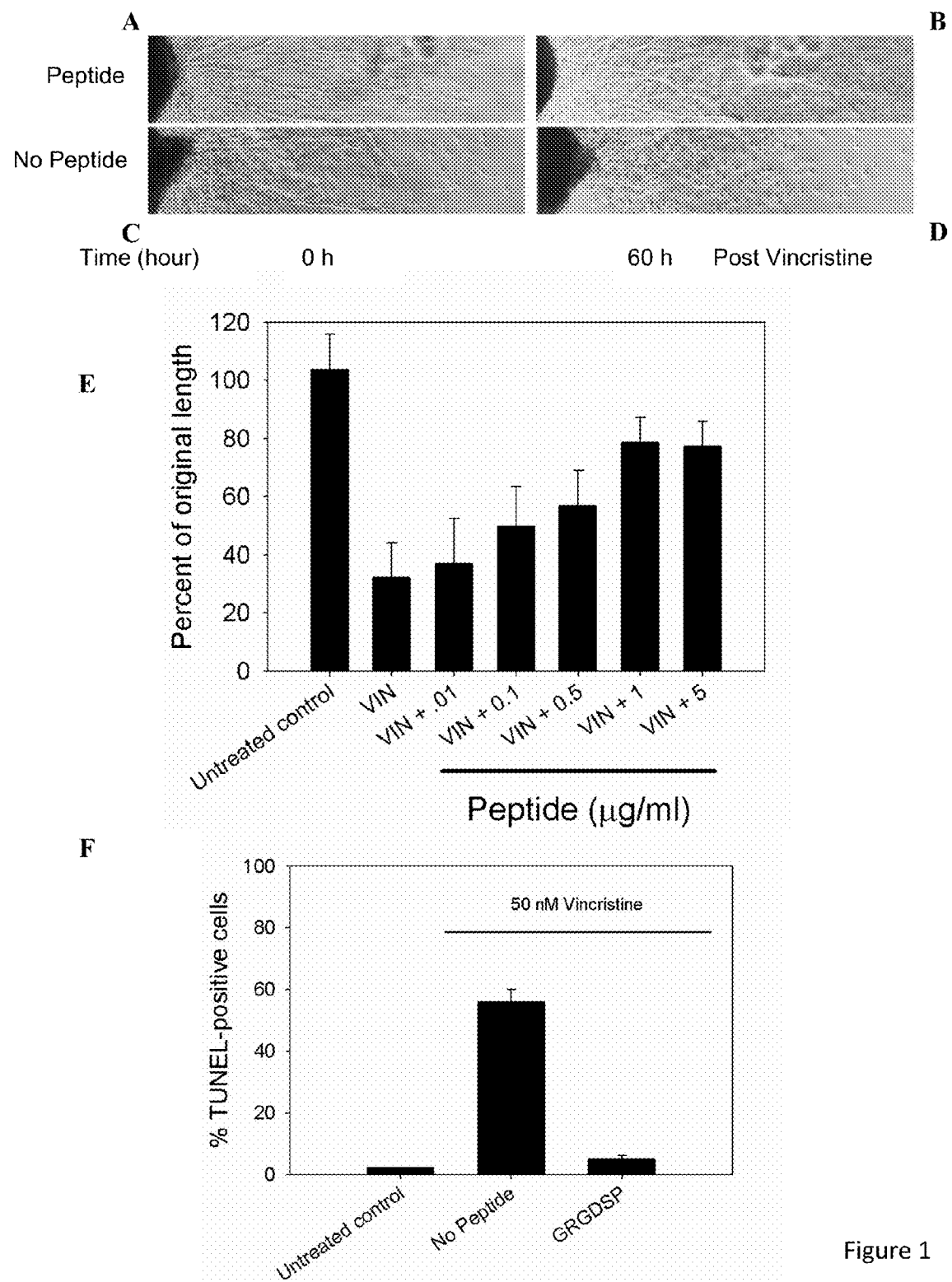
FIG. 1 shows axonal protection effected by RGD peptides in vitro. Panels A to D are representative images of dorsal root ganglion (DRG) explants after exposure to 50 nM vincristine at 0 and 60 hours. Explants in panels A and B were treated with 50 nM vincristine and 0.5 µg/ml peptide while those in panels C and D were treated with vincristine alone. Panel D shows almost complete axonal degeneration, but little axonal loss was seen in panel B. Panel E shows a dose-response curve of an RGD peptide's axonal protective effect against vincristine. Panel F shows that the axonal protection is associated with a marked decrease in neuronal death (TUNEL-postive cells). Panel G shows axonal protective effects provided by various RGD peptides. Panel H shows that the RGD peptides demonstrate a similar profound axonal protection activity in human embryonic stem cell-derived neurons.
Figure 1:
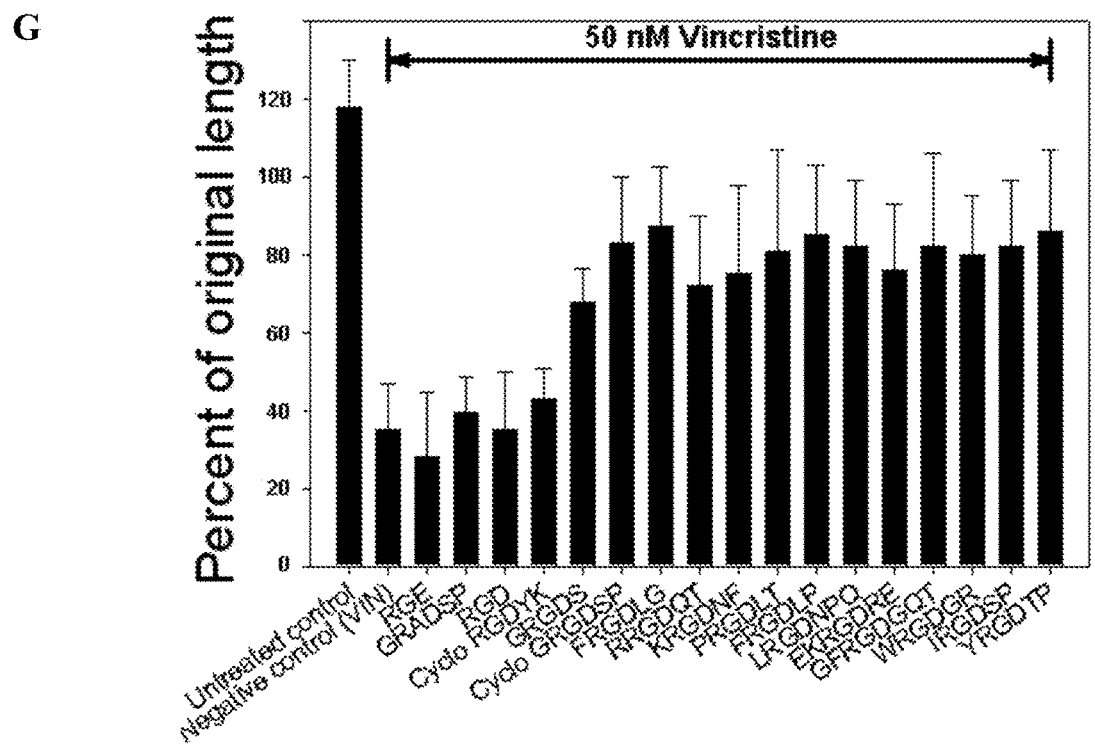
Figure 1:
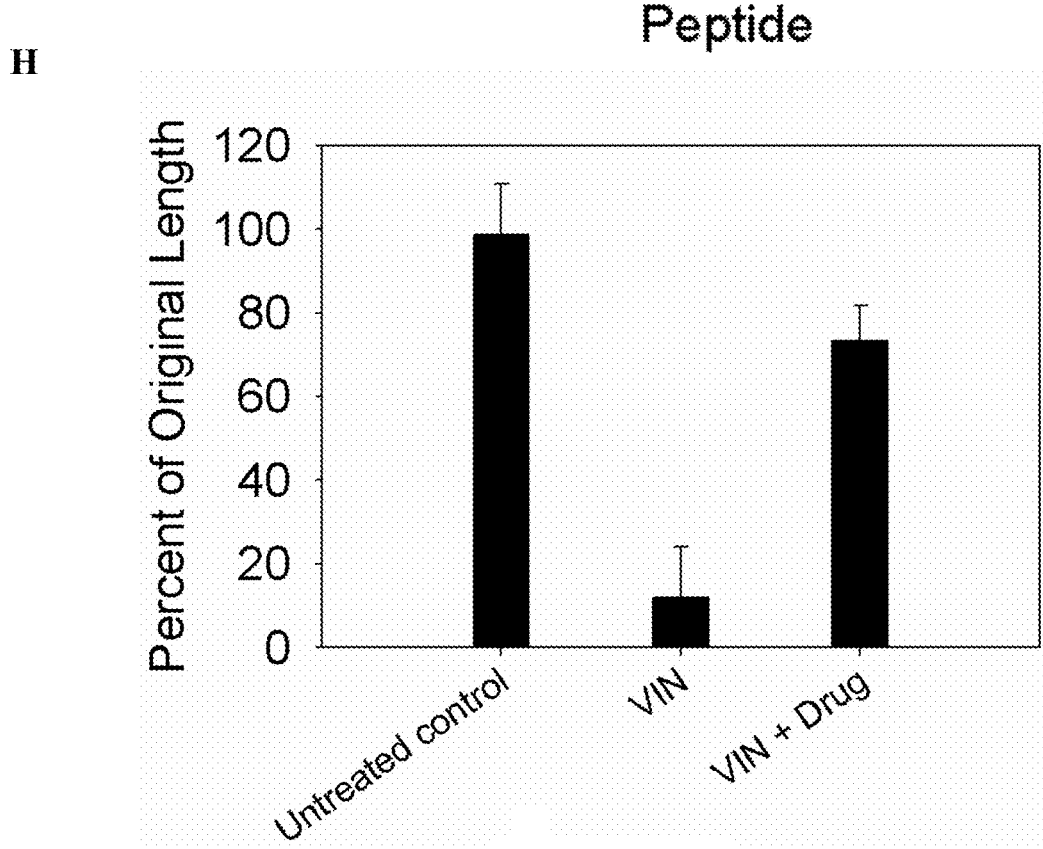

The present invention is directed toward compositions and methods for preventing neuronal and/or axonal degeneration, as well as compositions and methods for treatment of nerve injury, toxic insults and/or neurodegenerative disorders arising from such degeneration. The invention includes application of peptides containing the Arginine-Glycine-Aspartate (RGD) motif to neurons and/or axons.

The term "axonal degeneration" as used herein refers to the loss of functional activity and trophic degeneration of axons and their terminal arborizations. The term "neuronal degeneration" as used herein refers to the loss of functional activity and trophic degeneration of the cell bodies of the neurons. Prevention of degeneration is a different phenomenon from that of regeneration which refers to new growth and sprouting of new axonal or dendritic branches. Hence, degeneration and regeneration are opposing processes. Degeneration is often assessed as the degree of loss or death of axons and neurons, whereas regeneration is assessed as the degree of growth in new neurons and axonal length or sprouting.

The present inventors had previously reported that myelin-associated glycoprotein (MAG), a constituent of the adaxonal membrane of myelin-forming cells (MFC), promotes axonal stability and survival and that this protective effect depends on the presence of R-118 residue present in the RGD domain of MAG (Nguyen et al., 2009). The RGD tripeptide was originally identified as the sequence within fibronectin that mediates cell attachment. The RGD motif has been found in numerous other proteins and supports cell adhesion in many of these. The integrins, a family of cell-surface proteins, act as receptors for cell adhesion molecules. A subset of the integrins recognize the RGD motif within their ligands, the binding of which mediates both cell-substratum and cell-cell interactions. RGD peptides and mimetics, in addition to providing insights into the fundamental mechanisms of cell adhesion, are potential therapeutic agents for the treatment of diseases such as thrombosis and cancer.

The present invention is based on the surprising finding that small peptides containing the RGD sequence also possess the axonal and/or neuronal protective properties, similar to those exhibited by the full length MAG. A number of peptides of varying length comprising the RGD sequence were generated and their axonal and/or neuronal protective properties were tested. The addition of the peptides was sufficient to stabilize the axon and/or neuronal cell body and to prevent axonal/neuronal degeneration in vitro. This is described in detail in Example 1.

When C57Bl mice were given intraperitoneal injection of the RGD peptide cyclo-GRGDSP (SEQ ID NO:3) in normal saline, the peptide was detected in plasma at 30 and 60 min. While the levels in brain were only evident in the first hour, the peptide was detected in high concentration in the sciatic nerves at all time points up to 4 hours. This indicated that the RGD peptides can penetrate the nervous system at concentrations which had been shown to have protective effect in vitro. See Example 2.

Figure 2:
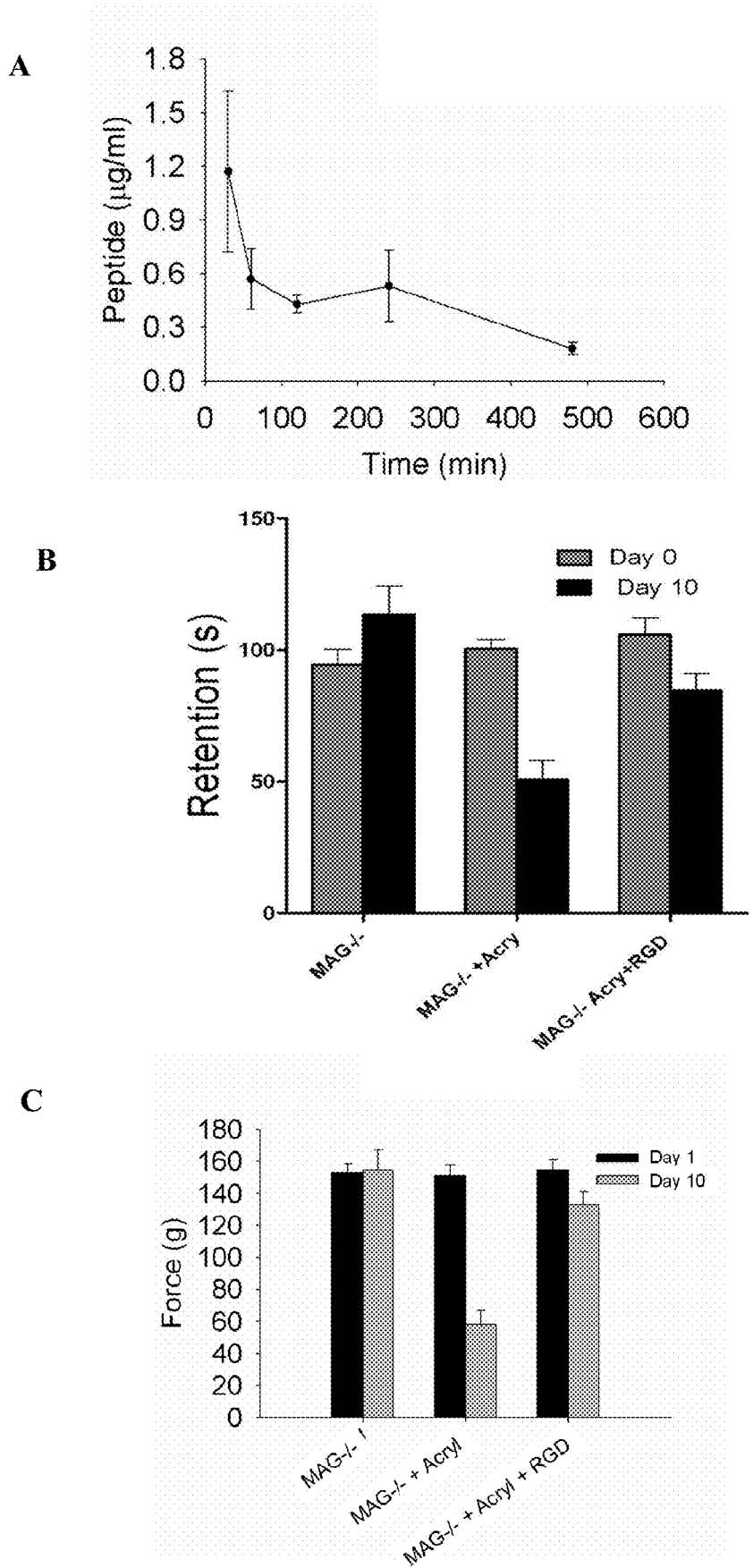
FIG. 2 shows axonal protection effected by RGD peptides in vivo. Panel A shows detection of peptide concentration in the sciatic nerve vs. time as quantified with the QTOF mass spectrometer following a single intravenous administration of 1 µg/g weight of peptide solution (n=5 mice). Panel B shows that on rotarod, the acrylamide intoxicated MAG–/– mice developed more rapid and severe motor impairment, which was largely prevented by the co-administration of an RGD peptide. (n=10 mice) Panel C shows that the administration of the peptide also prevented the decline in grip strength. Panel D shows that there was a 58% decrease in amplitudes of CMAP with acrylamide exposure at day 7 (gray). In contrast, there was no decrease with the co-administration of the peptide (n=10 mice). Panel E shows that there was significant denervation in acrylamide treated trembler-J mice, but this was largely prevented by co-administration of the peptide.
Figure 2:
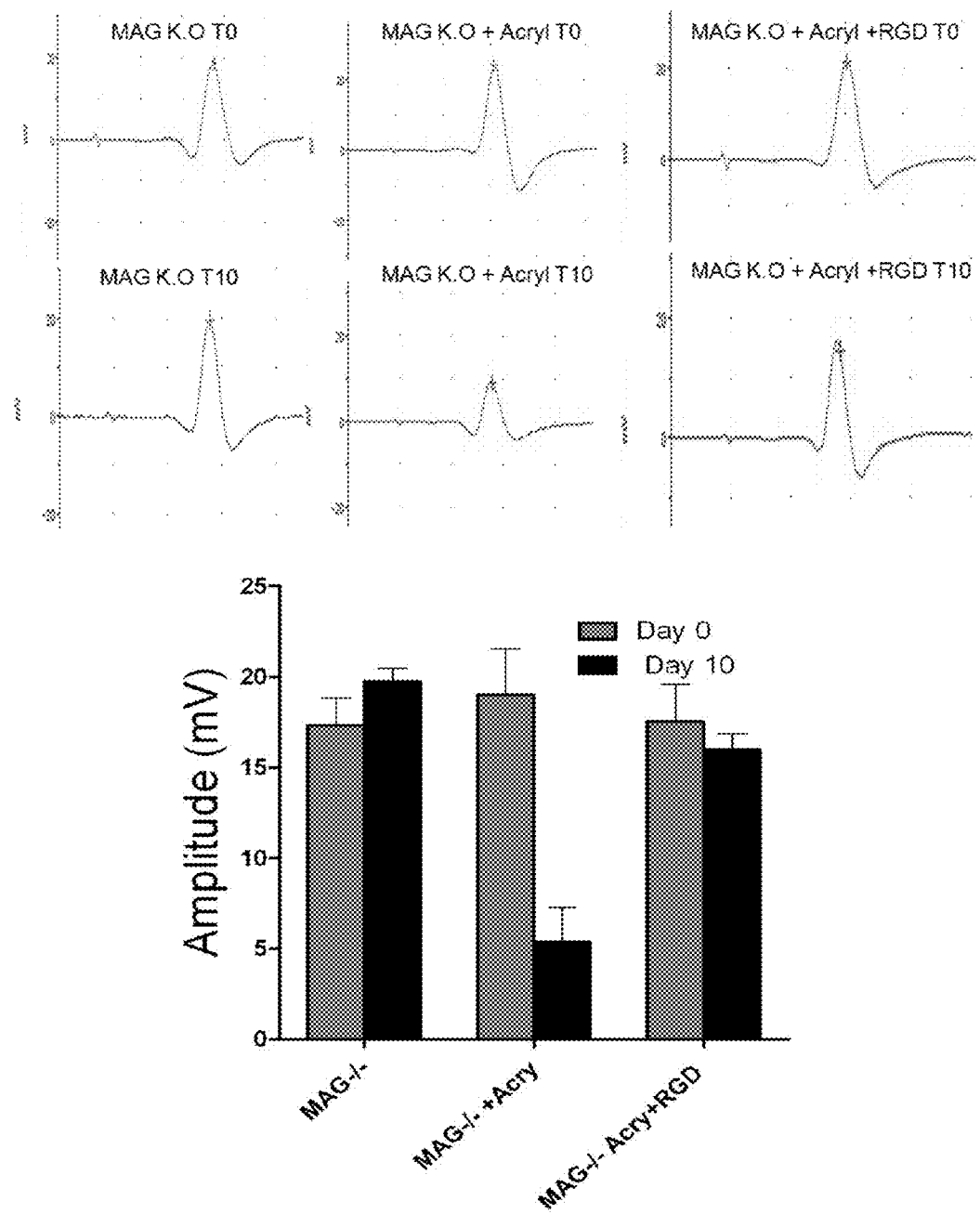
Figure 2:
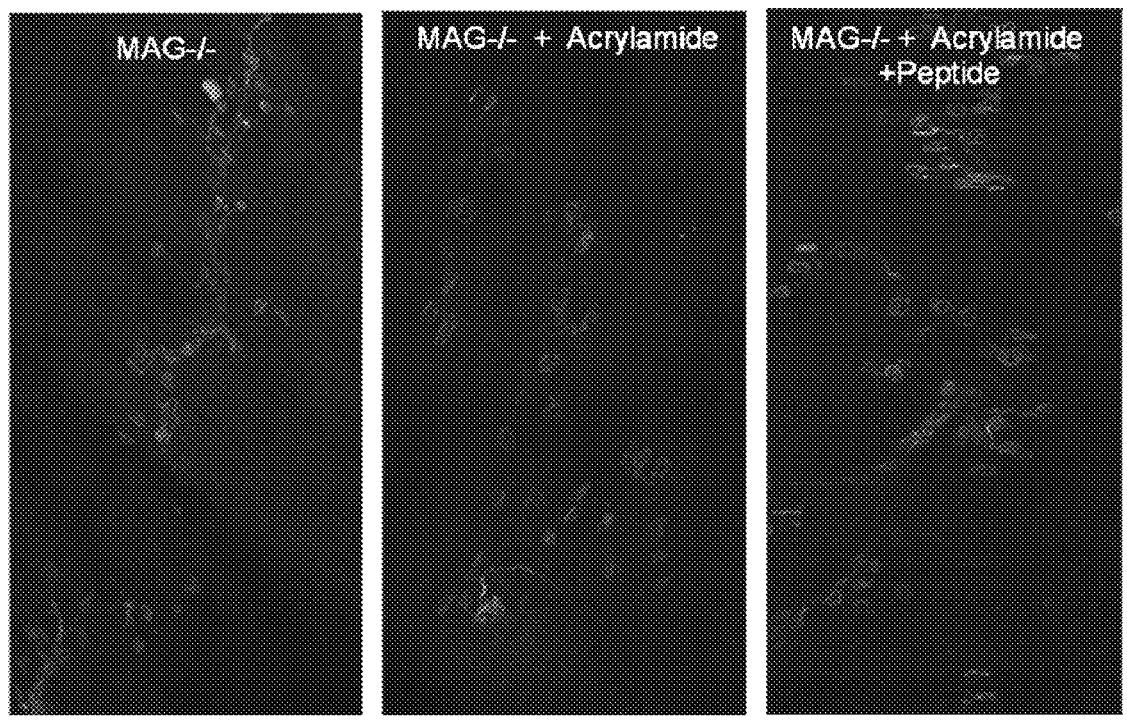

Furthermore, the RGD peptides can also prevent axonal and/or neuronal degeneration in vivo. See Example 3. Administration of acrylamide, a well characterized toxin, causes axonal "dying back" or degeneration without lymphocytic inflammatory response (Schaumburg et al., 1974, Ko et al., 2000; Ewaleifoh et al, 2012) in wild-type and MAG knockout mice. When MAG knockout mice were exposed to acrylamide for 10 days, they exhibited markedly impaired gait with marked sensory ataxia and spreading of the toes of the hind limbs. The acrylamide treated MAG–/– mice developed more rapid and severe motor impairment. Most mice fell off the rod even during pretraining and had profound decline in the retention time on the Rotarod (FIG. 2B). There was a decrease in amplitudes of CMAP (FIG. 2.D). Likewise, morphological analysis showed numerous axons in the skin with profound swelling, beading and segmentation consistent with pre-degenerative changes of Aβ fibers (FIG. 2.E) (Schaumburg et al., 1974, Hsieh et al., 1996, Ebenezer et al., 2007). In contrast, when the MAG–/– mice exposed to acrylamide were treated with daily intraperitoneal injection (IP) of the RGD peptides, the severe gait instability was largely prevented. In the RGD peptide treated mice, the profound axonal swelling, beading and segmentation consistent with pre-degenerative changes of Aβ fibers in the skin induced by acrylamide was also largely prevented. The neuromuscular junction morphology was normal. On gross observation, there was only mild gait unsteadiness. When challenged with the Rotarod test, acrylamide intoxicated MAG–/– mice who had received intraperitoneal injection of the RGD peptides had only mild difficulty in maintaining their balance on the rotating rods and had a similar retention time on the Rotarod in comparison with control MAG–/– mice. This was accompanied by little to no change in amplitudes of CMAP on electrophysiological testing. Thus, the RGD peptide was able to prevent significant axonal degeneration that is typically seen in MAG–/– mice treated with acrylamide. No adverse effect was observed with the administration of the peptides. The administration of the peptide also prevented the decline in grip strength (FIG. 2C).

Similar findings were also seen in other murine models such as Trembler J mice, a murine model of Charcot-Marie-Tooth type 1, MOG-EAE mice, model of multiple sclerosis with significant axonal loss, and Streptozotocin-induced diabetic mouse model. In all cases, intravenous or intraperitoneal daily injection of the RGD peptide cyclo-GRGDSP (SEQ ID NO:3) almost completely abolished the axonal/neuronal degeneration and behavioral deficits typically seen in these mouse models. Application of the RGD peptide allowed the diseased mice to have a normal or near normal phenotype similar to untreated wild-type animals. This data shows that RGD peptides are able to prevent axonal degeneration in vivo.

Accordingly, in one embodiment, the present invention includes a method of protecting axons and/or neurons from degeneration by contacting them with a composition containing a peptide that comprises the RGD amino acid sequence.

The composition of the present invention can also be applied to a wide variety of conditions involving axonal and neuronal degeneration, including nerve injury, toxic insults, and neurodegenerative diseases characterized by axonal and/or neuronal degeneration. As the efficacies of the RGD peptides have been shown in various mouse models of neurodegenerative diseases, they represent a novel set of neuroprotective agents to prevent axonal and/or neuronal degeneration in nerve injury, toxic insults, and neurodegenerative diseases. Accordingly in another embodiment, the present invention includes a method of preventing or treating axonal and/or neuronal degeneration in a subject who has or is at risk of having a nerve injury, toxic insult and/or neurodegenerative disorder. The method includes administering to the subject a composition containing a peptide that comprises the RGD sequence.

An acute neurodegenerative condition generally refers to a condition in which symptoms appear and change and/or worsen rapidly. These conditions are generally severe and sudden in onset. A chronic neurodegenerative condition generally develops and worsens over an extended period of time and is thus considered to be a long-developing condition. A traumatic neurodegenerative condition is a serious injury or shock to the body. Such conditions include but are not limited to traumatic brain injury, traumatic spinal cord injury, stroke, tethered spinal cord injury syndrome and global hypoxic ischemia. Toxic neurodegenerative condition is an exposure to drug (such as a chemotherapeutic drug) or toxic agents that cause nerve degeneration. In various embodiments of the present invention, practice of methods of the present invention will effectively treat the neurodegenerative condition. In the case of acute and chronic neurodegenerative conditions, effective treatment includes improving neurological function, stopping the decline in neurological function or slowing the decline in neurological function. In the case of traumatic neurodegenerative condition, methods of the present invention can stabilize a patient, alone or in combination with other treatments. In general, a traumatic neurological or neurodegenerative condition is stabilized when the condition no longer poses an immediate danger of death or harm to the patient and the patient's vital signs are stable (within normal limits).

Examples of neurodegenerative disorders include, without limitation, Charcot-Marie-Tooth (type 1 and type 6), multiple sclerosis, Alzheimer's disease, chronic spinocerebellar degeneration, diabetes, toxic injury, nerve injury, trauma, stroke, aging, brain ischemia, demyelinating disorder, Pakinson's disease, multiple system atrophy (MSA), polyneuropathy, motor neuron disease and dementia. The polyneuropathy may be toxic polyneuropathy, diabetic polyneuropathy, drug induced polyneuropathy, autoimmune polyneuroapthy, demyelinating polyneuropathy, or inherited polyneuropathy. The motor neuron disease may be amyotrophic lateral sclerosis (ALS), Huntington's disease or Spinal muscular atrophy. The dementia may be temporal dementia or lewy body dementia.

The present invention encompasses any peptide that comprises the RGD sequence. Such peptides may include one or more additional amino acids at the N terminal of the RGD sequence, at the C terminal of the RGD sequence, or both i.e. the RGD sequence may be flanked on either side by one or more amino acids. The length of the peptide may vary from about three amino acids to about one hundred amino acids. In some embodiments, the length of the peptide may be from about three to about fifty amino acids, from about three to about forty-five amino acids, from about three to about forty amino acids, from about three to about thirty-five amino acids, from about three to about thirty amino acids, from about three to about twenty-five amino acids, from about three to about twenty amino acids, or from about three to about fifteen amino acids. In some embodiments, the length of the peptide may be from about four amino acids to about ten amino acids. In some embodiments, the length of the peptide may be from about four amino acids to about eight amino acids. In some embodiments, the peptide may be about four, about five, about six, about seven, about eight, about nine or about ten amino acids in length. Particularly useful are the peptides that are able to cross the blood brain barrier in a mammal. The peptides of the present invention may be linear or cyclic. Cyclic peptides are molecules which have been modified to have a ring-shaped structure through the introduction of specific chemical bonds. These cyclic peptides possess attractive therapeutic properties including significantly improved biological activity and proteolytic stability. Peptides of the present invention can be cyclized as an end-to-end product, and the cyclization can be done between the N and C termini of the peptide. Peptides of the present invention can be cyclized using processes known in the art. (see, for example, Gentilucci et al. 2010. Chemical modifications designed to improve peptide stability: incorporation of non-natural amino acids, pseudo-peptide bonds, and cyclization. Current Pharmaceutical Design 16: 3185-3203; John S Davies. 2003. The cyclization of peptides and depsipeptides. Journal of Peptide Science 9: 471-501; and Meutermans et al. 2002. Synthesis of small cyclic peptides: An auxiliary approach to address the "difficult cyclization" problem. American Peptide Symposia 6 (4): 183-185).

Without limitation, examples of the RGD peptides of the present invention include the following sequences: RGDYK (SEQ ID NO:1), GRGDS (SEQ ID NO:2), GRGDSP (SEQ ID NO:3), FRGDLG (SEQ ID NO:4), RRGDQT (SEQ ID NO:5), KRGDNF (SEQ ID NO:6), PRGDLT (SEQ ID NO:7), FRGDLP (SEQ ID NO:8), FRGDSP (SEQ ID NO:9), LRGDNPQ (SEQ ID NO:10), EKRGDRE (SEQ ID NO:11), GFRGDGQT (SEQ ID NO:12), WRGDGR (SEQ ID NO:13), ARGDV (SEQ ID NO:14), IRGDSP (SEQ ID NO:15), CRGDNG (SEQ ID NO:16) and YRGDTP (SEQ ID NO:17).

In some preferred embodiments, the peptide may be GRGDS (SEQ ID NO:2), FRGDLG (SEQ ID NO:4), FRGDLP (SEQ ID NO:8), RRGDQT (SEQ ID NO:5), KRGDNF (SEQ ID NO:6), cyclo-RGDYK (SEQ ID NO:1), cyclo-IRGDSP (SEQ ID NO:15), cylco-FRGDSP (SEQ ID NO:9), cyclo-FRGDLP (SEQ ID NO:8) or cyclo-GRGDSP (SEQ ID NO:3).

The RGD peptides of the present invention further include variants of any of the foregoing amino acid sequences. Any amino acid substitution is permissible so long as the activity of the peptide is not significantly affected. In this regard, it is appreciated in the art that amino acids can be classified into groups based on their physical properties. Examples of such groups include, but are not limited to, charged amino acids, uncharged amino acids, polar uncharged amino acids, and hydrophobic amino acids. Preferred variants that contain substitutions are those in which an amino acid is substituted with an amino acid from the same group. Such substitutions are referred to as conservative substitutions.

Naturally occurring residues may be divided into classes based on common side chain properties:
  1) hydrophobic: Met, Ala, Val, Leu, Ile;
  2) neutral hydrophilic: Cys, Ser, Thr;
  3) acidic: Asp, Glu;
  4) basic: Asn, Gln, His, Lys, Arg;
  5) residues that influence chain orientation: Gly, Pro; and
  6) aromatic: Trp, Tyr, Phe.

For example, non-conservative substitutions may involve the exchange of a member of one of these classes for a member from another class.

In making amino acid changes, the hydropathic index of amino acids may be considered. Each amino acid has been assigned a hydropathic index on the basis of its hydrophobicity and charge characteristics. The hydropathic indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). The importance of the hydropathic amino acid index in conferring interactive biological function on a protein is generally understood in the art (Kyte et al., 1982, J. Mol. Biol. 157:105-31). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those within ±1 are particularly preferred, and those within ±0.5 are even more particularly preferred.

It is also understood in the art that the substitution of like amino acids can be made effectively on the basis of hydrophilicity, particularly where the biologically functionally equivalent protein or peptide thereby created is intended for use in immunological embodiments, as in the present case. The greatest local average hydrophilicity of a protein, as governed by the hydrophilicity of its adjacent amino acids, correlates with its immunogenicity and antigenicity, i.e., with a biological property of the protein. The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4). In making changes based upon similar hydrophilicity values, the substitution of amino acids whose hydrophilicity values are within ±2 is preferred, those within ±1 are particularly preferred, and those within ±0.5 are even more particularly preferred. One may also identify epitopes from primary amino acid sequences on the basis of hydrophilicity.

Desired amino acid substitutions (whether conservative or non-conservative) can be determined by those skilled in the art at the time such substitutions are desired. Exemplary amino acid substitutions are shown below in Table 1.

TABLE 1

Amino Acid Substitutions

| Original Amino Acid | Exemplary Substitutions |
| --- | --- |
| Ala | Val, Leu, Ile |
| Arg | Lys, Gln, Asn |
| Asn | Gln |
| Asp | Glu |
| Cys | Ser, Ala |
| Gln | Asn |
| Glu | Asp |
| Gly | Pro, Ala |
| His | Asn, Gln, Lys, Arg |
| Ile | Leu, Val, Met, Ala |
| Leu | Ile, Val, Met, Ala |
| Lys | Arg, Gln, Asn |
| Met | Leu, Phe, Ile |
| Phe | Leu, Val, Ile, Ala, Tyr |
| Pro | Ala |
| Ser | Thr, Ala, Cys |
| Thr | Ser |
| Trp | Tyr, Phe |
| Tyr | Trp, Phe, Thr, Ser |
| Val | Ile, Met, Leu, Phe, Ala |

Conservative substitutions typically include substitutions within the following groups: glycine and alanine; valine, isoleucine and leucine; aspartic acid, glutamic acid, asparagine, and glutamine; serine and threonine; lysine and arginine; and phenylalanine and tyrosine. Substitutions may also be made on the basis of conserved hydrophobicity or hydrophilicity (Kyte and Doolittle, J. Mol. Biol. (1982) 157: 105-132), or on the basis of the ability to assume similar polypeptide secondary structure (Chou and Fasman, Adv. Enzymol. (1978) 47: 45-148, 1978).

The RGD peptides further include an amino acid sequence that is at least about 60% identical, at least about 65% identical, at least about 70% identical, at least about 75% identical, at least about 80% identical, at least about 85% identical, at least about 90% identical, at least about 91% identical, at least about 92% identical, at least about 93% identical, at least about 94% identical, at least about 95% identical, at least about 96% identical, at least about 97% identical, at least about 98% identical, at least about 99% identical to an amino acid sequence to any of the foregoing amino acid sequences.

The RGD motif is known to bind to the integrin receptor. The addition of the peptides of the present invention to primary DRG neuronal cultures induced rapid phosphorylation of neurofilament (NFH), change in NAD synthase nicotinamide mononucleotide adenylyltransferase (NM-NAT) expression, and focal adhesion kinase (FAK), an integrin-linked kinase, at the tyrosine 397 residue (Y397), which are indicative of integrin binding to a ligand. Co-administration of echistatin or specific function-blocking antibody to β1-integrin abolished the axonal/neuronal protective ability of the peptide. See Example 1. Without intending to be bound by theory, these results indicate that the RGD peptides exert their protective effect by binding to the β1-integrin receptor.

In some embodiments, the RGD peptides of the present invention may be chemically modified to provide a more potent and longer lasting molecule. For example, the RGD peptides may be PEGylated (covalent attachment of polyethylene glycol polymer chains to prolong its circulatory time and aid uptake into tissues). Other modifications include, without limitation, cyclization, N-terminal acetylation, C-terminal amidation, N-methylation, phosphorylation of amino acids, and peptide biotinylation. The methods of such modifications are known to those of skill in the art and are incorporated herein.

In some embodiments, the RGD peptides may comprise one or more modified amino acids. Examples of such amino acids, include without limitation, D-amino-acids, L-beta-homo amino acids, D-beta-homo amino acids, and N-methylated amino acids.

In some embodiments, the RGD peptides may contain a fluorescent label. Addition of a fluorescent label allows for easy detection of the peptide. In general, the preferred fluorescent labels should have high fluorescence quantum yields and retain the biological activities of the unlabeled peptides. A fluorescent label or fluorophore can be attached to the peptide at a specific point through a covalent bond, which is stable and not destructive under most biological conditions. In some cases, a functional linker may be introduced between the fluorescent label and the peptide to minimize the alteration of peptide's biological activity. A number of fluorescent labels are known in the art and are commercially available. All such labels are encompassed in the present invention.

In some embodiments, the composition of the present invention may further include a pharmaceutically acceptable carrier (including an excipient, diluent, adjuvant or delivery vehicle). The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Common suitable pharmaceutical carriers are described in "Remington's Pharmaceutical Sciences" by E. W. Martin.

The amount of composition to be administered generally comprises a therapeutically effective amount of the composition, that is, an amount effective to prevent, ameliorate, lessen or inhibit the axonal and/or neuronal degeneration. Such amounts typically comprise from about 0.1 to about 1,000 mg of the compound per kilogram of body weight of the mammal to which the composition is administered. Therapeutically effective amounts can be administered according to any dosing regimen satisfactory to those of ordinary skill in the art.

The compositions can be formulated for a particular type or route of delivery, if desired, including for parenteral or transmucosal, (e.g., orally, nasally or transdermally). Parenteral routes include intravenous, intra-arteriole, intramuscular, intradermal, subcutaneous, intraperitoneal, intraventricular and intracranial administration. In some embodiments, the mode of administration may be oral, parenteral, subcutaneous and intravenous.

In some embodiments, the therapeutic composition of the invention can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss: New York, pp. 353-365 (1989). To reduce its systemic side effects, this may be a preferred method for introducing the compound.

In yet another embodiment, the therapeutic composition can be delivered in a controlled release system. For example, a peptide may be administered using intravenous infusion with a continuous pump, in a polymer matrix such as poly-lactic/glutamic acid (PLGA), a pellet containing a mixture of cholesterol and the anti-amyloid peptide antibody compound (U.S. Pat. No. 5,554,601) implanted subcutaneously, an implantable osmotic pump, a transdermal patch, liposomes, or other modes of administration.

The compositions of the invention may further comprise a therapeutically effective amount of another agent or therapeutic compound, preferably in respective proportions such as to provide a synergistic effect with the present invention. Alternatively, the composition of the invention can be administered concurrently with or sequentially with another pharmaceutical composition comprising such other therapeutic agent or compound. A therapeutically effective amount of a composition of the invention relates generally to the amount needed to achieve a therapeutic objective.

In some embodiments of the invention, the step of administering is conducted after the occurrence of a traumatic neurological condition. In some embodiments, the step of administering is conducted as shortly after the incident causing the traumatic neurological condition as possible. For example, the step of administering can be conducted within about 1 hour, 2 hours, 3 hours, 4 hours, 5 hours, 6 hours, 9 hours, 12 hours, 18 hours or 24 hours after the incident. In other embodiments, the step of administering is conducted at longer times after the incident causing the traumatic neurological condition, and the method is still effective. For example, the administration can be initiated after about 1 day, 2 days, 3 days, 4 days, 5 days, 6 days, 7 days, 8 days, 9 days, 10 days, 20 days or 30 days and at more extended sub-acute (1 month) and long term chronic time points after the occurrence of the traumatic neurological condition. In still other embodiments, the administration is initiated at significantly longer times after the occurrence of a traumatic neurological or neurodegenerative condition. For example, the administration can be initiated after about 1 month, 3 months, 6 months, 1 year, 3 years, 5 years, 7 years, or 9 years after the occurrence of the traumatic neurological condition.

In still other embodiments, the step of administering may be conducted by administering a bolus of the composition to the patient and/or continuous delivery of the composition to the patient over a period of time, such as over about 1 hour, about 2 hours, about 3 hours, about 4 hours, about 5 hours, about 6 hours, about 9 hours, about 12 hours, about 15 hours, about 18 hours, about 21 hours, about 24 hours or over a period of 8 days.

Other embodiments of the present invention comprise treating a nerve injury, toxic insult or neurodegenerative disorder by administering a composition containing an RGD peptide in combination with an additional treatment for a neurodegenerative condition. In a preferred embodiment, the additional treatment may comprise administering anti-inflammatory agents, temperature reducing agents, immobilization, cell transplantation based therapies, cell infusion based therapies, implantation of biomaterials, exercise and functional electrical stimulation based rehabilitative therapies, surgical interventions, clinically induced hypothermia based CNS therapies and gene therapy based interventions. Anti-inflammatory agents are well known in the art and include but are not limited to non-steroidal anti-inflammatory drugs (NSAIDS) such as aspirin, ibuprofen and naproxen, and analgesics such as acetaminophen. Temperature reducing agents are also well known in the art and may include ibuprofen and acetaminophen.

In some embodiments of the present invention, treating a neurodegenerative condition can include, in addition to the administration of a composition comprising RGD peptide, administration of a second therapeutic compound for treating the neurodegenerative condition. Such second therapeutic compounds can be a second composition comprising another RGD peptide that is different from the first RGD peptide, anti-inflammatory agents, temperature reducing agents, chondroitinase enzymes, neurotrophic growth factors designed to promote axon growth or remyelination of axons, and anti-apoptotic agents to promote survival of CNS neurons and glia and combinations thereof.

In embodiments of the present invention, the present methods can result in recovery of neurological function in the patient. In yet other embodiments, the methods can result in one or more of the following indications, compared to a control, suppression of axonal and neuronal loss or death, prevention of dysfunction and atrophy of the central and peripheral nervous system, an increase in axon extension and branching, upregulation of NMNAT, suppression of the synthesis of signals and molecules associated with axonal and neuronal degeneration and apoptosis, suppression of synthesis of caspase, suppression of the axon growth inhibitory actions of signals and molecules associated with axonal and neuronal degeneration and apoptosis, suppression of inflammation, suppression of astrogliosis, suppression of aberrant expression of multiple axonal and neuronal toxic molecules, and de-sensitization of axons and neurons to the influence of axonal toxic molecules within the injured or diseased adult mammalian nervous system in order to prevent cell death and to promote plasticity and function of neural circuits.

The following examples are provided for the purposes of illustration and are not intended to limit the scope of the present invention.

EXAMPLES

Example 1

This example demonstrates that RGD peptides provide axonal protection and prevent axonal and neuronal degeneration in vitro.

Several small RGD peptides containing RGD sequence were generated and their axonal protective effect was tested. The RGD peptides included RGDYK (SEQ ID NO:1), GRGDS (SEQ ID NO:2), FRGDLG (SEQ ID NO:4), FRGDSP (SEQ ID NO:9), IRGDSP (SEQ ID NO:15), RRGDQT (SEQ ID NO:5), KRGDNF (SEQ ID NO:6), PRGDLT (SEQ ID NO:7) in linear as well as cyclo forms. The addition of these five to eight amino acid peptides were sufficient to stabilize the axon and to prevent axonal/neuronal death in postnatal (P4-5) dorsal root ganglion (DRG) and cerebrocortical neurons in vitro (FIG. 1).

DRG explants were exposed to 50 nM vincristine. Results are shown in FIG. 1. Explants in panels A and B were treated with 50 nM vincristine and 0.5 µg/ml RGD peptide while those in panels C and D were treated with vincristine alone. FIG. 1E shows data related to application of cyclo-GRGDSP (SEQ ID NO:3). The cyclo-GRGDSP (SEQ ID NO:3) peptide potently promoted axonal survival in cell culture with EC50=0.5 µM (FIG. 1.E). The axonal protection is associated with a marked decreased in neuronal death (TUNEL-postive cells (FIG. 1.F).

The protective effect of the DRG peptides was dependent upon their ability to bind to β1-integrin receptor. The addition of the peptide to primary DRG neuronal cultures also induced rapid phosphorylation of neurofilament (NFH), change in MNAT and focal adhesion kinase (FAK), an integrin-linked kinase, at the tyrosine 397 residue (Y397), indicative of integrin binding to a ligand. Co-administration of specific function-blocking antibody to β1-integrin abolished the axonal protective ability of the GRGDSP (SEQ ID NO:3) peptide.

Example 2

This example illustrates that injected RGD peptides effectively penetrate the peripheral nervous system of a mammal.

To test the bioavailability and bio-distribution of the RGD peptides in vivo, C57Bl mice were given intraperitoneal injection of 1 µg/g weight of cylco-GRGDSP (SEQ ID NO:3) in normal saline (1 mg/ml). The mice were sacrificed at 30, 60, 120, and 240 minutes. Blood, brain, skin, muscle, and tibial and sciatic nerves were collected. The presence of the peptide was detected using LC-QTOF mass spectrometer.

The peptide was detected in plasma at 30 and 60 minutes. Levels in brain were evident within 60 minutes. However, the peptide was detected in high concentration in the sciatic nerves at all time points up to 4 hours. See FIG. 2A. This indicates that peptide can penetrate the peripheral nerve at concentrations which had been shown to have axonal protective effect in vitro.

Example 3

This example illustrates that RGD peptides provide axonal protection and prevent axonal degeneration in vivo.

To test that RGD peptides may prevent axonal degeneration in a murine model, acrylamide, a well characterized toxin causing axonal "dying back" or degeneration without lymphocytic inflammatory response (Schaumburg et al., 1974, Ko et al., 2000, Ewaleifoh et at, 2012), was administered to wild-type and MAG–/– mice. When MAG knockout mice at 6 weeks of age were exposed to acrylamide for 10 days, there was markedly impaired gait with marked sensory ataxia and spreading of the toes of the hind limbs. The acrylamide treated MAG–/– mice developed more rapid and severe motor impairment. Most mice fell off the rod even during pretraining and had profound decline in the retention time on the Rotarod (FIG. 2B). There was a 68% decrease in amplitudes of CMAP (FIG. 2.D). Likewise, morphological analysis showed numerous axons in the skin with profound swelling, beading and segmentation consistent with pre-degenerative changes of Aβ fibers (FIG. 2.E) (Schaumburg et al., 1974, Hsieh et al., 1996, Ebenezer et al., 2007).

In contrast, when the MAG–/– mice exposed to acrylamide were treated with daily intraperitoneal injection (IP) of the RGD peptides (e.g., cyclo-GRGDSP (SEQ ID NO:3), cyclo-FRGDSP (SEQ ID NO:9), cyclo-FRGDLP (SEQ ID NO:8), or cyclo-IRGDSP (SEQ ID NO:15)) the severe gait instability was largely prevented (FIG. 2B). In these peptide treated mice, the profound axonal swelling, beading and segmentation consistent with pre-degenerative changes of Aβ fibers in the skin induced by acrylamide was also largely prevented (FIG. 2E). The neuromuscular junction morphology was normal (FIG. 2E). On gross observation, there was only mild gait unsteadiness. When challenged with the Rotarod test, acrylamide intoxicated MAG–/– mice with intraperitoneal injection of the RGD peptides had mild difficulty in maintaining their balance on the rotating rods and had a similar retention time on the Rotarod in comparison with control MAG–/– mice (FIG. 2B). This was accompanied by little to no change in amplitudes of CMAP on electrophysiological testing (FIG. 2D). The administration of the peptide also prevented the decline in grip strength (FIG. 2C). This shows that the RGD peptide can prevent significant axonal degeneration that is typically seen in MAG–/– mice treated with acrylamide.

Similar findings were also seen in other murine models including (1) Trembler J mice, a murine model of Charcot-Marie-Tooth type 1, (2) MOG-EAE mice, model of multiple sclerosis with significant axonal loss, and (3) Streptozotocin-induced diabetic mouse model. In all cases, intravenous or intraperitoneal daily injection of the cylco-GRGDSP (SEQ ID NO:3) or cyclo-IRGDSP (SEQ ID NO:15) almost completely abolished the axonal/neuronal degeneration and behavioral deficits typically seen in these mouse models. The RGD peptide allowed the diseased mice to have a normal or near normal phenotype similar to untreated wild-type animals. These data show that RGD peptides prevent axonal degeneration in vivo.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims. All publications and references are herein expressly incorporated by reference in their entirety.

What is claimed is:

1. A method of treating axonal and/or neuronal degeneration in a subject who has a condition involving axonal and/or neuronal degeneration, comprising administering to the subject a composition comprising a peptide, wherein the peptide is cyclic, is six amino acids in length and comprises the amino acid sequence RGDSP (SEQ ID NO:18) or RGDLP (SEQ ID NO:19), wherein administration of the composition is sufficient to treat the axonal and/or neuronal degeneration in the subject.

2. The method of claim 1, wherein the RGD sequence is capable of binding to beta-1-integrin protein.

3. The method of claim 1, wherein the condition is selected from the group consisting of nerve injury, toxic insult and neurodegenerative disorders.

4. The method of claim 3, wherein the condition is a neurodegenerative disorder selected from the group consisting of: Charcot-Marie-Tooth, multiple sclerosis, Alzheimer's disease, chronic spinocerebellar degeneration, diabetes, stroke, brain ischemia, demyelinating disorder, polyneuropathy, Parkinson's disease, multiple system atrophy (MSA), motor neuron disease, dementia, and combinations thereof.

5. The method of claim 4, wherein the Charcot-Marie-Tooth is selected from the group consisting of Charcot-Marie-Tooth type 1 and type 6.

6. The method of claim 4, wherein the polyneuropathy is selected from the group consisting of Toxic polyneuropathy, diabetic polyneuropathy, drug induced polyneuropathy, autoimmune polyneuropathy, demyelinating polyneuropathy, and inherited polyneuropathy.

7. The method of claim 4, wherein the motor neuron disease is selected from the group consisting of amyotrophic lateral sclerosis (ALS), Huntington's disease and Spinal muscular atrophy.

8. The method of claim 4, wherein the dementia is selected from the group consisting of temporal dementia and lewy body dementia.

9. The method of claim 3, wherein the condition is a nerve injury.

10. The method of claim 3, wherein the condition is a toxic insult.

11. The method of claim 1, wherein the peptide comprises an amino acid sequence selected from the group consisting of GRGDSP (SEQ ID NO:3), FRGDLP (SEQ ID NO:8), FRGDSP (SEQ ID NO:9), and IRGDSP (SEQ ID NO:15).

12. The method of claim 11, wherein the peptide is selected from the group consisting of IRGDSP (SEQ ID NO:15) and GRGDSP (SEQ ID NO:3).

13. The method of claim 1, wherein the peptide is subjected to a modification selected from the group consisting of pegylation, N-methylation, phosphorylation of amino acids, and peptide biotinylation.

14. The method of claim 1, wherein the peptide comprises a fluorescent label.

15. The method of claim 1, wherein the peptide comprises one or more modified amino acids.

16. The method of claim 15, wherein the one or more modified amino acids are selected from the group consisting of D-amino-acids, L-beta-homo amino acids, D-beta-homo amino acids, N-methylated amino acids, and combinations thereof.

17. The method of claim 1, wherein the composition further comprises a pharmaceutically acceptable carrier.

18. The method of claim 1, wherein the subject is a mammal.

19. The method of claim 1, wherein the step of administering is by a mode of administration selected from the group consisting of oral, parenteral, subcutaneous and intravenous administration.

20. A method of protecting axons and/or neurons from degeneration, comprising contacting the axons and/or neurons with a composition comprising a peptide, wherein the peptide is cyclic, is six amino acids in length and comprises the amino acid sequence RGDSP (SEQ ID NO:18) or RGDLP (SEQ ID NO:19), wherein the contacting with the composition is sufficient to protect the axons and/or neurons from degeneration.

21. The method of claim 20, wherein the RGD sequence is capable of binding to beta-1-integrin protein.

22. The method of claim 20, wherein the peptide comprises an amino acid sequence selected from the group consisting of GRGDS (SEQ ID NO:2), GRGDSP (SEQ ID NO:3), FRGDLP (SEQ ID NO:8), FRGDSP (SEQ ID NO:9), and IRGDSP (SEQ ID NO:15).

23. The method of claim 22, wherein the peptide is selected from the group consisting of GRGDS (SEQ ID NO:2), FRGDLP (SEQ ID NO:8), cyclo-IRGDSP (SEQ ID NO: 15), cyclo-FRGDSP (SEQ ID NO:9), cyclo-FRGDLP (SEQ ID NO:8) and cyclo-GRGDSP (SEQ ID NO:3).

24. The method of claim 20, wherein the peptide is subjected to a modification selected from the group consisting of pegylation, N-methylation, phosphorylation of amino acids, and peptide biotinylation.

25. The method of claim 20, wherein the peptide comprises a fluorescent label.

26. The method of claim 20, wherein the peptide comprises one or more modified amino acids.

27. The method of claim 26, wherein the one or more modified amino acids are selected from the group consisting of D-amino-acids, L-beta-homo amino acids, D-beta-homo amino acids, N-methylated amino acids, and combinations thereof.

* * * * *